United States Patent [19]
Walloch

[11] Patent Number: 5,337,750
[45] Date of Patent: Aug. 16, 1994

[54] AUTOMATIC BLOOD PRESSURE MONITOR EMPLOYING ARTIFACT REJECTION METHOD AND APPARATUS

[75] Inventor: Richard A. Walloch, Aloha, Oreg.

[73] Assignee: SpaceLabs Medical, Inc., Redmond, Wash.

[21] Appl. No.: 922,201

[22] Filed: Jul. 30, 1992

[51] Int. Cl.$^5$ ............................................. A61B 05/00
[52] U.S. Cl. .................................. 128/680; 128/681; 364/413.03
[58] Field of Search ............................... 128/677–686; 364/413.03

[56] References Cited

U.S. PATENT DOCUMENTS

| | | | |
|---|---|---|---|
| 4,360,029 | 11/1982 | Ramsey, III | 128/682 |
| 4,408,614 | 10/1983 | Weaver et al. | 128/680 |
| 4,543,962 | 10/1985 | Medero et al. | 128/682 |
| 4,889,133 | 12/1989 | Nelson et al. | 128/681 |
| 4,949,710 | 8/1990 | Dorsett et al. | 128/681 |
| 4,974,597 | 12/1990 | Walloch | 128/680 |
| 4,984,577 | 1/1991 | Frankerester | 128/681 |

FOREIGN PATENT DOCUMENTS

0029349 11/1980 European Pat. Off. ....... A61B 5/02

Primary Examiner—Lee S. Cohen
Assistant Examiner—Robert L. Nasser, Jr.
Attorney, Agent, or Firm—Seed and Berry

[57] ABSTRACT

A blood pressure monitor capable of measuring blood pressure in the presence of artifact. One embodiment of the blood pressure monitor uses a detector to generate a trigger signal on the occurrence of the R-wave or other point on the ECG waveform. Oscillometric waveform samples taken at the same time after each trigger signal are then summed with each other over many heartbeats to generate an average oscillometric waveform that is used to determine blood pressure by conventional means. Another embodiment of the blood pressure monitor stores oscillometric waveform samples over many heartbeats. The monitor then assumes that the period of the heartbeat has a variety of durations, and it derives respective sets of composite samples by summing the stored samples having the same temporal relationship to the start of each assumed period. The set of composite samples corresponding the a waveform that best matches an actual oscillometric wave is then used to determine blood pressure by conventional means.

22 Claims, 8 Drawing Sheets

AUTOMATIC BLOOD PRESSURE MONITOR EMPLOYING ARTIFACT REJECTION METHOD AND APPARATUS

TECHNICAL FIELD

This invention relates to automatic blood pressure monitors, and more particularly, to an automatic blood pressure monitor minimizing the deleterious effects of artifacts.

BACKGROUND OF THE INVENTION

Automatic blood pressure monitors are commonly used to periodically measure the blood pressure of a patient. In most automatic blood pressure monitors, a pressure cuff is attached to a patient's arm over the brachial artery. The cuff is first pressurized with an applied pressure that is high enough to substantially occlude the brachial artery. The cuff pressure is then gradually reduced, either continuously or in increments. As the pressure is reduced to systolic pressure, the flow of blood through the brachial artery beneath the cuff increases substantially.

When the blood flows through the brachial artery following each contraction of the heart, it imparts a pulsatile movement to the wall of the artery. This pulsatile movement is coupled to a blood pressure cuff extending over the artery as minute changes in the cuff pressure, which are known as oscillometric pulses. Automatic blood pressure monitors employing the oscillometric method measure and record the amplitude of the oscillometric pulses at a number of cuff pressures. After the blood pressure measurement had been completed, a table contains the oscillometric pulse amplitudes recorded at each cuff pressure.

In theory, the systolic, diastolic, and mean arterial blood pressures can then be determined from the values in the table using theoretical and/or empirical definitions of these parameters as a function of the amplitudes of these oscillometric pulses. However, blood pressure measurements are often adversely affected by artifact, generally produced by patient movement. Motion-induced artifact can substantially alter the measured amplitude of oscillometric pulses thus introducing inaccuracies in the measurement of the patient's blood pressure.

The use of "signal averaging" is a conventional technique to extract periodic signals in the presence of random noise. It is used in many fields, both medical and non-medical. Within medicine, signal averaging is most often used to extract neural evoked potentials. A number of commercial blood pressure monitors average an attribute of the oscillometric pulse, usually pulse amplitude, to eliminate artifacts. For example, the averaging of oscillometric peak amplitudes to replace a value judged to be artifact is mentioned in U.S. Pat. Nos. 4,754,761 and 4,638,810 to Ramsey, 4,799,492 to Nelson, and 4,190,886 to Sherman.

A number of conventional devices use the QRS-complex of the ECG to help eliminate artifacts from blood pressure measurements. The QRS-Complex is the portion of the ECG that represents the contraction of the ventricles of the heart. Most of these devices use a technique called "ECG-Gating". By ECG-Gating, blood pressure signals are accepted only when they appear in a specified temporal relationship to the QRS complex. None of these prior art devices use the QRS-Complex to average the input data. Moreover, these prior art devices using ECG-Gating are auscultatory rather than oscillometric. Auscultatory methods for blood pressure measurement rely upon the detection of the Korrotkoff sounds just as the physician depends upon these sounds when he or she uses a stethoscope.

U.S. Pat. No. 4,860,759 to Kahn mentions the QRS-Complex in describing a non-invasive blood pressure monitor. However, the QRS-Complex is not actually used by the monitor in connection with making blood pressure measurements. Kahn does use a pulse sensor located on a finger distal to the blood pressure cuff to determine blood pressure. However, averaging techniques are not used. The pulse sensor merely detects blood flow through the cuff just as a physician uses Korrotkoff sounds to indicate that blood flow.

U.S. Pat. No. 4,974,597 to Walloch discloses a blood pressure monitor that uses the QRS-Complex to detect artifacts. Again averaging techniques are not used. The QRS-Complexes are used to bracket the time period during which a single oscillometric pulse or Korrotkoff sound is expected.

U.S. Pat. No. 4,677,984 to Shramek discloses using the time between the QRS-Complex and the detection of a pulsatile pressure change beneath the cuff to reconstruct the waveform of the inter-arterial pressure wave. Again averaging is not involved.

It has not heretofore been realized that useful oscillometric waveforms can be extracted from artifact by averaging all of the data points of the oscillometric waveform rather than just a single attribute of that waveform.

SUMMARY OF THE INVENTION

The primary object of the invention is to generate accurate indications of blood pressure in the presence of artifact.

This and other objects of the invention are accomplished by a blood pressure monitor having a unique signal processor which is used with conventional components of a blood pressure monitor such as a blood pressure cuff communicating with an air pump, an air valve, and a pressure transducer. The signal processor sums samples of the transducer output taken after one heartbeat with samples of the transducer output taken at corresponding times after a plurality of other heartbeats to obtain composite samples of the oscillometric waveform over a plurality of heartbeats. The composite samples are then analyzed at a plurality of cuff pressures to determine blood pressure.

In one embodiment of the invention the blood pressure monitor further includes a trigger signal generator that produces a trigger signal having a predetermined temporal relationship to each heartbeat. The signal processor then derives the composite samples by summing the digital samples taken after each trigger signal with correspondingly ordered digital samples taken after respective other trigger signals.

The signal processor can process the digital samples either for a predetermined number of heartbeats at each of a plurality of different pressures or until the difference between a composite sample derived after a heartbeat and the corresponding composite sample derived after the previous heartbeat is less than a predetermined value.

In another embodiment of the invention the blood pressure monitor further includes an analog-to-digital converter for sampling the output of the transducer and generating digital samples corresponding thereto. The signal processor stores these digital samples for a plurality of heartbeats, and processes the stored samples by assuming that the period of the patient's heartbeat has a variety of durations. The signal processor processes the stored samples by sequentially deriving sets of tentative composite samples, each of which correspond to the sum of digital samples having the same temporal relationship with the start of a respective assumed period between heartbeats. The signal processor continues to generate these sets of tentative composite samples using different assumed periods between heartbeats until the waveform corresponding to a set of tentative composite samples for an assumed period correspond to an actual oscillometric waveform. The signal processor then determines blood pressure by analyzing the tentative composite samples corresponding to the actual oscillometric waveform in a conventional manner.

The signal processor can employ a variety of techniques to determine that a set of tentative composite samples for an assumed period correspond to an actual oscillometric waveform. For example, the signal processor can determine if the oscillometric waveform corresponding to the tentative composite samples is periodic, has a single major peak, or conforms to a template of samples corresponding to an actual oscillometric waveform.

DETAILED DESCRIPTION OF THE INVENTION

Figure 1:
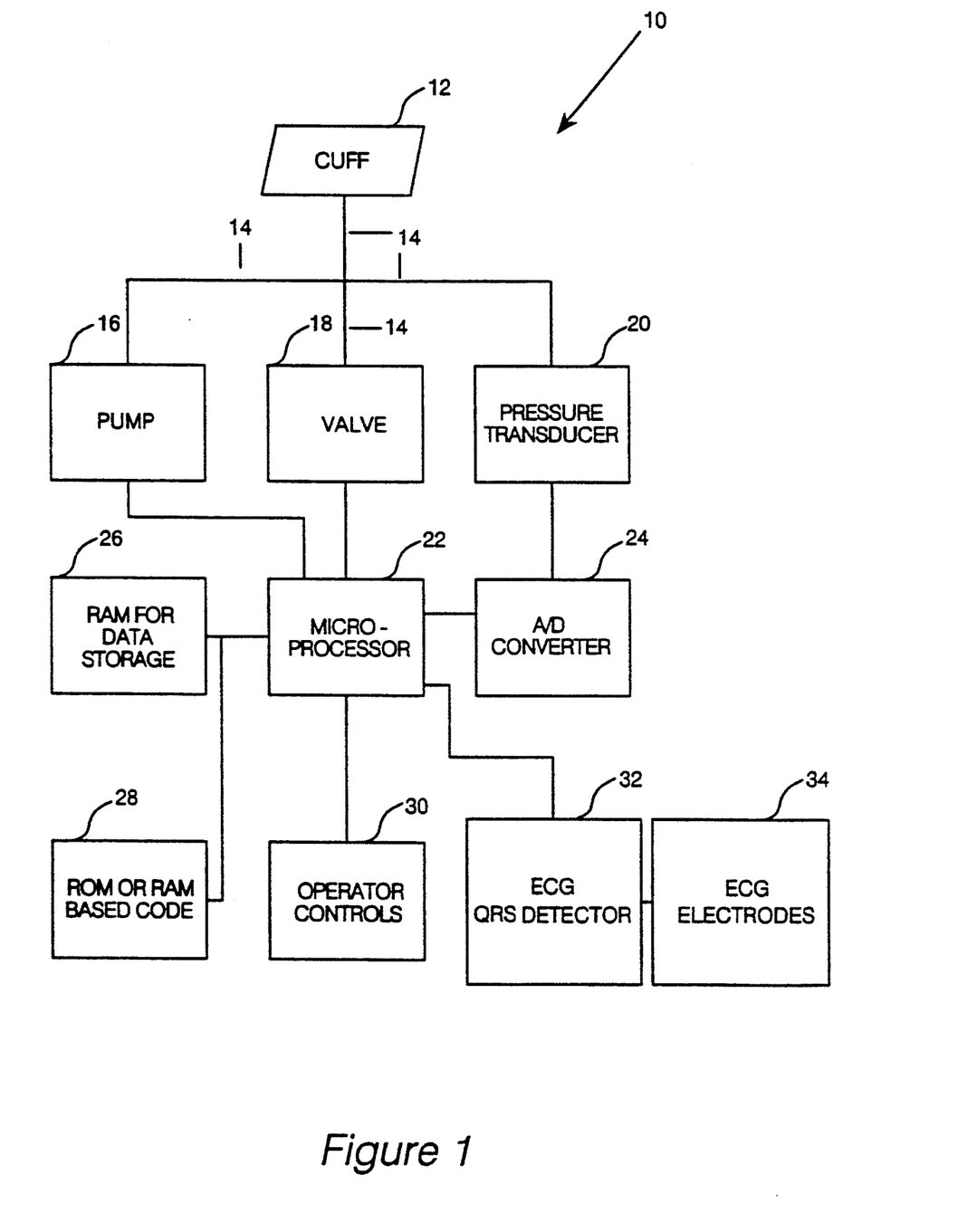
FIG. 1 is a block diagram of a presently preferred embodiment of an automatic blood pressure monitor having means for rejecting artifact induced measurement errors.

One embodiment of an automatic blood pressure monitor 10 using the inventive artifact rejection method and apparatus is illustrated in FIG. 1. The system is composed of a number of hardware components, all of which are conventional. The system includes a conventional blood pressure cuff 12 in fluid communication through tubes 14 with a conventional pump 16, a conventional solenoid valve 18, and a conventional pressure transducer 20. The pump 16 and solenoid valve 18 are electrically connected to respective output ports of a conventional microprocessor 22 which controls the operation of the pump 16 and solenoid valve 18.

During the operation of the automatic blood pressure measuring system, the pump 16 inflates the blood pressure cuff 12 to a pressure that is greater than the expected systole, as indicated by the pressure transducer 20. The solenoid valve 18 is then opened, usually for a predetermined period, although it may be continuously open to allow a slight leakage of air from the blood pressure cuff 12. However, the solenoid valve 18 normally allows air to escape from the cuff 12 fairly rapidly in relatively small increments. As the pressure in the cuff 12 is reduced, either gradually or incrementally, the pressure in the cuff 12 is measured by the pressure transducer 20.

The pressure in the blood pressure cuff 12 consists of two components, namely, a relatively constant, or "DC", component and a relatively variable, or "AC", component. The relatively constant component determines the occlusive force of the blood pressure cuff 12. The relatively variable component is produced by the minute change in the pressure of the cuff 12 following each contraction of the heart. Thus, the relatively constant DC component of the pressure in the cuff can be used as an indication of cuff pressure, while the relatively variable AC component of the pressure in the cuff 12 can be used as an indication of an oscillometric pulse.

A signal from the pressure transducer 20 is supplied to a conventional analog-to-digital ["A/D"] converter 24, where it is digitized for use by the microprocessor 22. In many modern blood pressure devices, the A/D converter 24 is actually contained on the microprocessor chip. Whether the A/D converter 24 is on the microprocessor chip or whether it is located on a separate chip, the microprocessor 22 has access to a digitized signal indicative of the output from the pressure transducer 20.

The microprocessor 22 extracts the two components of the pressure in the blood pressure cuff namely (a) the pressure within the cuff and (b) the minute change in the pressure of the cuff following each contraction of the heart. Alternatively, separation of the cuff pressure into these two components can be accomplished by external hardware filters, as is quite common in older automatic blood pressure monitors. Whether the separation is accomplished by external hardware filters or by an algorithm internal to the microprocessor is not important for the current invention.

As mentioned above, the microprocessor 22 is of conventional variety and, as is typical with such devices, is connected to a random access memory 26, used for the storage of data, and to either random access memory or read-only memory 28, that contains the software for operating the microprocessor 22. Operator controls 30 such as a keyboard or buttons, are also connected to the microprocessor 22.

As mentioned above, one embodiment of the inventive artifact rejection method and apparatus uses a trigger signal which occurs once each heartbeat. In order to supply this trigger signal, conventional ECG electrodes 34 record the electrical signals from the patient's heart. The QRS-complex is the easily recognized portion of the patient's ECG which indicates the contraction of the heart's ventricles. This QRS-complex is detected by a conventional QRS Detector 32 which may be implemented by either hardware or a combination of hardware and software. The QRS Detector 32 outputs an indicating signal to the microprocessor 22 through a bus upon each occurrence of the QRS-complex. In some applications, the same microprocessor that controls the blood pressure algorithm may also extract the QRS-complex from the ECG. Although the QRS-complex is the largest and most easily detected portion of the ECG, other portions of the ECG could also serve as a trigger. Moreover, other triggers are possible, such as a pulse detector on the finger or other limb of the patient. Finally, as mentioned above, one embodiment of the inventive artifact rejection method and apparatus does not require the use of a trigger signal.

As explained above, the microprocessor 22 is controlled by software that is stored as a series of program instructions in the memory 26. A flow chart from which object code can be easily and quickly written by one skilled in the art is illustrated in FIGS. 2 through 6.

Figure 2:
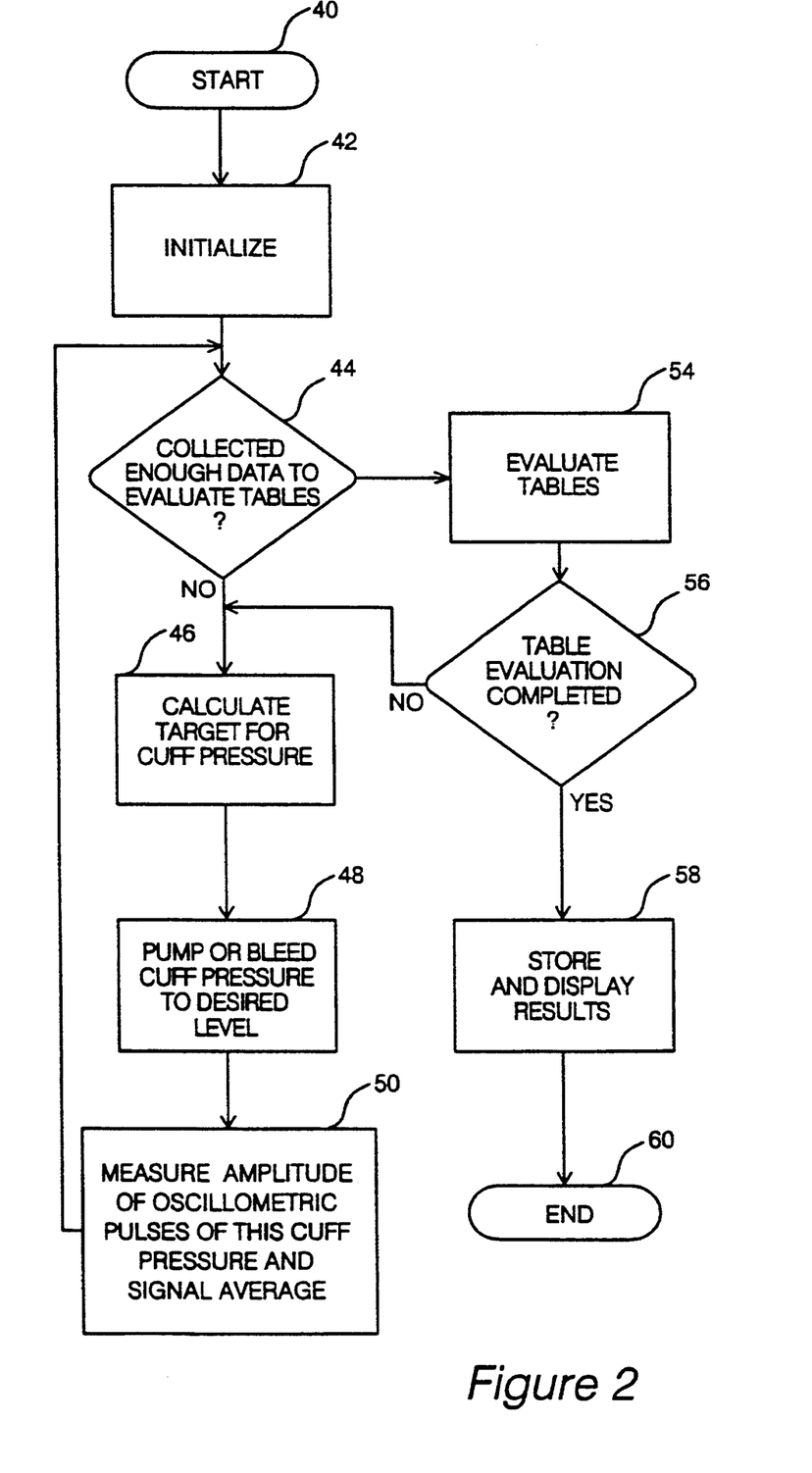
FIG. 2 is a flow chart of a main computer program used to program a microprocessor used in the automatic blood pressure monitor of FIG. 1.

With reference to FIG. 2, a main program starts at 40 either through an operator command, automatically at power-up or when call by another program stored in the memory 26. As is conventional with microprocessor-based systems, the microprocessor 22 (FIG. 1) is initialized at 42 to set up the software for subsequent processing, such as, for example, by establishing tables that subsequently will contain data, by setting flags, and by setting variables to known values. The program then checks at 44 to determine if enough oscillometric pulse amplitude data have been collected in oscillometric data tables for evaluation. The decision block 44 is first encountered prior to obtaining any oscillometric pulse amplitude data. Thus, when the program initially encounters decision block 44, the tables will not contain enough data to be evaluated. As a result, the program will branch to 46 to calculate a target value for the pressure in the blood pressure cuff 12 (FIG. 1). The target pressure for the cuff 12 will, of course, be in excess of the cuff pressure before the measurement is started. The microprocessor 22 then energizes the pump 16 (FIG. 1) at 48 while the output of the pressure transducer 20 is digitized by the analog-to-digital convertor 24. The frequency of the digitization is controlled in a conventional manner by a conventional clock driven interrupt routine (not shown). A conventional filtering algorithm may be applied to the digitized signal in order to eliminate random noise from the resulting cuff pressure. The microprocessor 22 continues to energize the pump 16 at 48 until the cuff pressure is equal to the target pressure. On subsequent passes through steps 46 and 48, the target pressure calculated at 46 will be lower than the pressure in the cuff 12, so that the microprocessor 22 will energize the solenoid valve 18 at 48 to reduce the pressure in the cuff 12 to the target pressure.

The program progresses from step 48 in FIG. 2 to step 50, where pressure transducer data samples are collected and averaged at the current cuff pressure. This process of data sample collection and averaging will be more fully described below.

When sufficient data are collected and averaged at a given cuff pressure, the program returns to 44 where it once again decides whether or not enough data have been collected to evaluate the tables. The answer once again will be negative on the second pass though step 44. Therefore, the program will then loop through 44, 46, 48, and 50 until sufficient data are collected. Each time the program proceeds through 46 and 48, the pressure in the cuff is decreased, usually in fixed steps.

Once the program decides at step 44 that sufficient data are collected, it branches to 54 where the tables are evaluated. A decision is made at step 56 as to whether or not the table evaluation is complete. If the table evaluation is complete, the program branches to 58 where the results are displayed and stored. The main program then ends at 60. If the program decides at step 56 that sufficient data had not been obtained to complete the table evaluation, then the program branches back to step 46. The program then completes the loop 48, 50, 44 to collect additional data.

Figure 3:
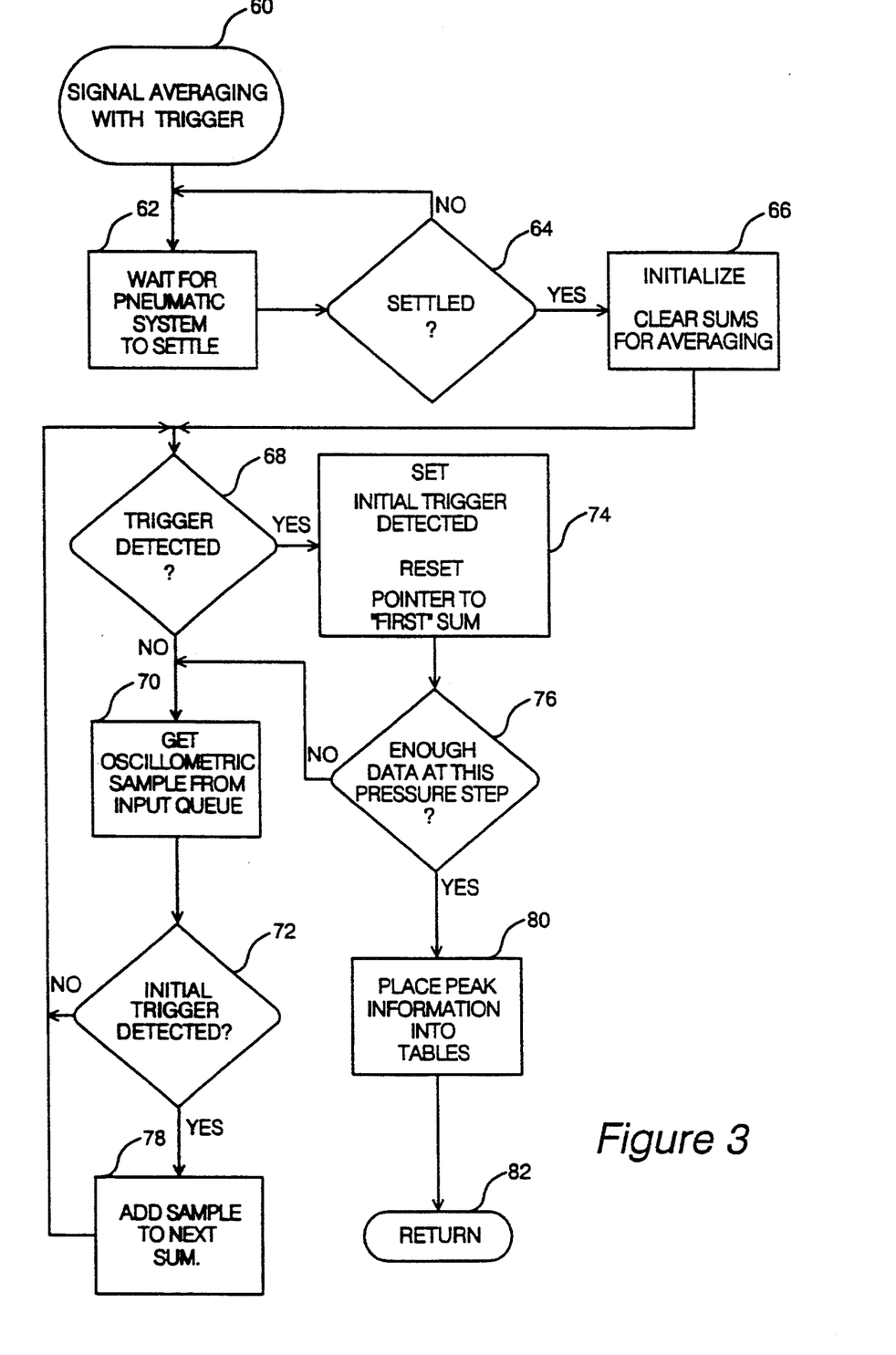
FIG. 3 is one embodiment of a signal averaging subroutine called by the main computer program shown in FIG. 2.

One embodiment of the signal collection and averaging step 50 is shown in FIG. 3. The signal collection and averaging step 50 is accomplished by a subroutine which is entered at 60 each time the pressure in the cuff is changed. The program then waits at step 62 for pressure fluctuations to settle that are introduced in the pneumatics during each pump or bleed. The program checks at step 64 to determine whether these pressure fluctuations have subsided. The check may be merely the passage of a set amount of time or it could be a function of the cuff pressure measurements. The program simply loops through steps 62 and 64 until the pneumatic system is settled.

Once the pneumatic system has settled, the program branches to step 66, where variables are initialized for averaging in a conventional manner. The arrays into which individual samples will be summed and an INITIAL TRIGGER DETECTED flag are also cleared in this step 66.

The subroutine determines at step 68 whether or not a trigger has been detected. In the preferred embodiment, the trigger is the occurrence of an QRS complex on the ECG which may be generated by the QRS Detector 32 (FIG. 1). A trigger and an oscillometric pulse are both generated by each heartbeat so that the trigger should be synchronized to the occurrence of the oscillometric pulse. Furthermore, corresponding samples of different oscillometric pulses should follow the respective trigger for each oscillometric pulse by the same time delay. In other words, the oscillometric pulse samples following each trigger should form substantially the same waveform as a function of the time from the occurrence of the trigger.

Although the occurrence of the trigger will be synchronous with each heartbeat, it will be asynchronous with the program. Therefore, most often the decision will be "NO" the first time the program reaches step 68, i.e. when the program reach 68 a trigger will not have occurred already. As a result, the subroutine will retrieve an oscillometric pulse sample from an input queue (not shown) in step 70.

The oscillometric pulse input queue is simply a set of oscillometric pulse samples that have been stored in either the microprocessor 22 or the memory 28 in response to a conventional clock driven interrupt service routine (not shown). The interrupt service routine causes the microprocessor 22 to read the analog to digital converter 24 and place the digitized oscillometric pulse sample into a memory. The memory is preferably read in a "first in, first out" manner, thus forming a data queue.

Usually, the first time the program reaches 72, the INITIAL TRIGGER DETECTED flag will still be false. Therefore, the program will branch or loop back to step 68. This causes the sample which was obtained from the queue in step 74 to be discarded because block 78, which uses that sample, is not reached. The reason for discarding the sample is that it does not bear any predetermined temporal relationship to a trigger, and is thus irrelevant. The program continues to loop through 68, 70 and 72 until a trigger is detected.

Eventually a trigger is detected at 68. The program then branches from step 68 to step 74 where the INITIAL TRIGGER DETECTED flag is set to true. Setting this flag true will result in later oscillometric samples being used by the program because the program will thereafter branch from step 72 to 78. Unlike the samples occurring before a trigger and discarded at step 72, these later oscillometric pulse samples are used because they bear a predetermined temporal relationship to the trigger. As explained in greater detail below, those samples will be averaged with corresponding samples of other oscillometric pulses in order to make a blood pressure measurement.

A pointer is also reset at 74, which will cause the next sample obtained to be designated as the first sample of an oscillometric pulse. This sample is stored in an array of oscillometric pulse samples. As explained in greater detail below, after the next trigger is detected, the first sample of the next oscillometric pulse is summed with the first sample of the previous oscillometric pulse. As a result, the array of oscillometric pulse samples eventually contains a sum of corresponding oscillometric pulse samples corresponding in number to the number "N" of triggers that have been detected before the subroutine determines at step 76 that enough data has been obtained at the current cuff pressure. The average value of oscillometric pulse at the point in time corresponding to a given sample can then be calculated simply by dividing by the number "N."

The first time the program reaches step 76, it branches to 70 because enough data will not have been collected at the current pressure step.

The program now branches through 70, 72, 78, and 68 until the next trigger is detected. Each time through this loop, a subsequent sample of the oscillometric pulse is summed in the array with the corresponding oscillometric pulse samples of respective prior oscillometric pulses. When each succeeding trigger is detected at 68, the pointers to the array of sums is reset so that the next sample received is added to the first element of the array. The flag INITIAL TRIGGER DETECTED is also set each time the program passes through 74. However, this has no effect because that flag remains set until it is initialized at 66 on a subsequent pressure step.

The following table may better illustrate the above-described process of sample averaging. Although in actual practice hundreds if not thousands of samples may occur between triggers, the present example will assume only 4 samples occur for the sake of brevity and clarity. Also, the samples from a large number of oscillometric pulses may be summed with each other. However, in this example, the samples from only 4 oscillometric pulses will be summed with each other. In the following table the numbers for the samples are normalized oscillometric pulse amplitudes, and the designation "T" designates the occurrence of a trigger in the sequence of samples.

| SAMPLES | T | 2 | 3 | 7 | 5 | T | 4 | 3 | 8 | T | 3 | 4 |
|---------|---|---|---|---|---|---|---|---|---|---|---|---|
|         |   | 7 | 3 | T | 4 |   |   |   |   |   |   |   |

In the sequence above, four samples—2,3,7,5—follow the first trigger, three samples—4,3,8—follow the second trigger, four samples—3,4,7,3—follow the third trigger, and one sample—4—follows the fourth trigger. These samples would be summed in the above-described array as follows:

TABLE 1

| | | | | |
|---|---|---|---|---|
| 1ST TRIGGER SAMPLES | 2 | 3 | 7 | 5 |
| 2ND TRIGGER SAMPLES | 4 | 3 | 8 | |
| 3RD TRIGGER SAMPLES | 3 | 4 | 7 | 3 |
| 4th Trigger SAMPLE | 4 | | | |
| AVERAGE | 3.25 | 3.3 | 7.3 | 4.0 |

Starting with the first sample after the first trigger—"2," each sample is added to the next element of the array of sums, until the next trigger occurs. The second trigger sample "4" is added to the first trigger sample "2" because both are the first sample after a trigger. The second trigger sample "3" is added to the first trigger sample "3" because both are the second sample after a trigger. etc. The averages of the sums are then calculated by dividing the sums by the number of triggers, although in some algorithms, the sums themselves can be used.

The program continues to loop through 68, 70, 72, 74, 76, and 78 until the program decides at step 76 that a sufficient number of oscillometric pulses have been sampled at the current cuff pressure. Although there are many possible methods that can be used to make this decision, some of these methods are:

1. The simplest method is to wait until a given number of triggers have been obtained.
2. A more complex method is to compare the averages obtained after N triggers with those averages that were previously collected with N-1 triggers. As more samples are added to each sum, the averages will vary less as each new sample is added.
3. A combination of the two above methods is preferably used.

Once the decision that sufficient samples have been averaged at 76, the program branches to 80 where the information about the averaged oscillometric waveform is extracted and made available for other portions of the program. The extraction of the information about the peak is conventional in that the amplitude, rise time and other conventional aspects of the peak are measured. The passing of that information to the rest of the program either on the stack or in special locations is also conventional.

The program continues to loop through 44, 46, 48, and 50 (FIG. 2) until there are sufficient data in the oscillometric tables to permit the table evaluation. Then the program branches to 54 where the tables are evaluated. At 56, the table evaluation is judged to be either complete or incomplete. If incomplete, the program branches at 56 to 46 in order to collect more data.

If the table evaluation is judged to be complete at 56, then the program branches to 58. The table evaluation could have resulted either in either (a) a blood pressure measurement, or (b) an indication that there were too many artifacts to obtain a blood pressure measurement. In any event, the program displays and stores the results at 58. The program can also adjust parameters, such as screening and trigger levels, which may aid in the collection of the next blood pressure at this time. The main program then ends usually by returning to the calling procedure 60.

Figure 4:
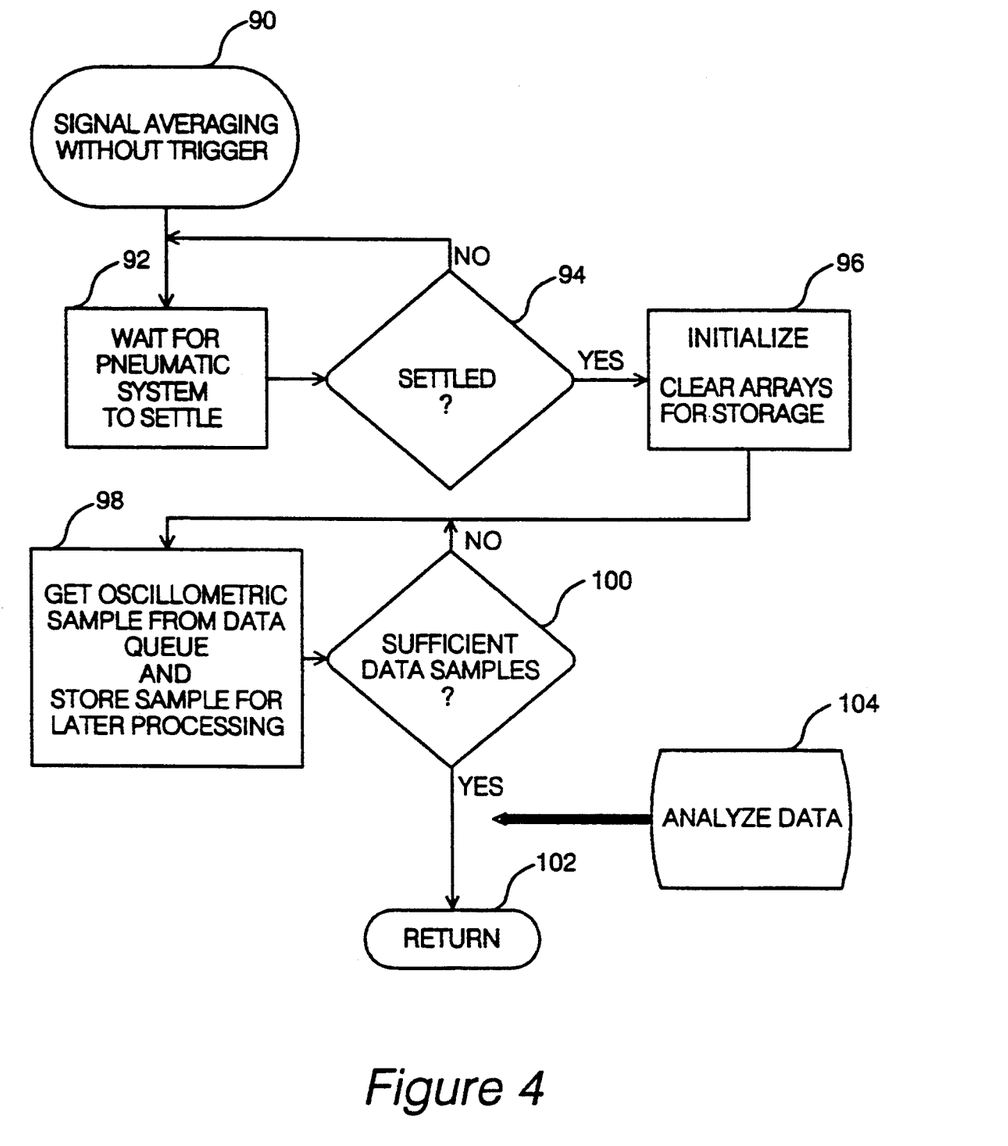
FIG. 4 is another embodiment of a signal averaging subroutine called by the main computer program shown in FIG. 2.

An alternative subroutine for performing the signal collection and averaging step 50 (FIG. 2) is illustrated in FIG. 4. This subroutine of FIG. 4 is able to average corresponding samples of successive oscillometric pulses without the need to use a trigger to designate which samples correspond to each other.

With reference to FIG. 4, in a manner that is similar to the subroutine of FIG. 3, the alternative subroutine enters the signal averaging routine at 90 and then loops through 92 and 94 until the pneumatic system has settled. When settled, the program branches to step 96 were buffers are initialized for storage. In the subroutine of FIG. 3, arrays of sample sums were also cleared at the step 66 corresponding to step 96. However, in the embodiment of FIG. 4, each individual sample—instead of a sample sum—is stored in an array. Thus, the arrays for the subroutine of FIG. 4 will be substantially larger than the sample sum array generated in the subroutine of FIG. 3.

The subroutine then retrieves each sample from an input queue at 98 and stores that sample for later averaging. As in the subroutine of FIG. 3, the oscillometric pulse input queue is simply a set of oscillometric pulse samples that have been stored in either the microprocessor 22 (FIG. 1) or the memory 28 in response to a conventional clock driven interrupt service routine (not shown). The interrupt service routine causes the microprocessor 22 to read the analog to digital converter 24 and place the digitized oscillometric pulse sample into a memory. The memory is preferably read in a "first in, first out" manner, thus forming a data queue.

After each sample had been retrieved from an input queue at 98, the program loops between 98 and 100 until a sufficient number of samples have been collected. Then the program branches to return to the calling program at 102.

Logically, one might expect a step 104 to analyze the data collected between steps 100 and 102. However, it is preferable to analyze the data asynchronously when the main program of FIG. 2 and the subroutine of FIG. 3 or 4 is being performed at the next (generally lower) cuff pressure. When the subroutine is looping through 98 and 100, most of the time will be spent waiting for the next sample. This "wait" time can be used to analyze the data that had been collected at the previous pressure step. This practice of storing data and subsequently analyzing it is conventional and well known by anyone skilled in the art of programming.

Figure 5:
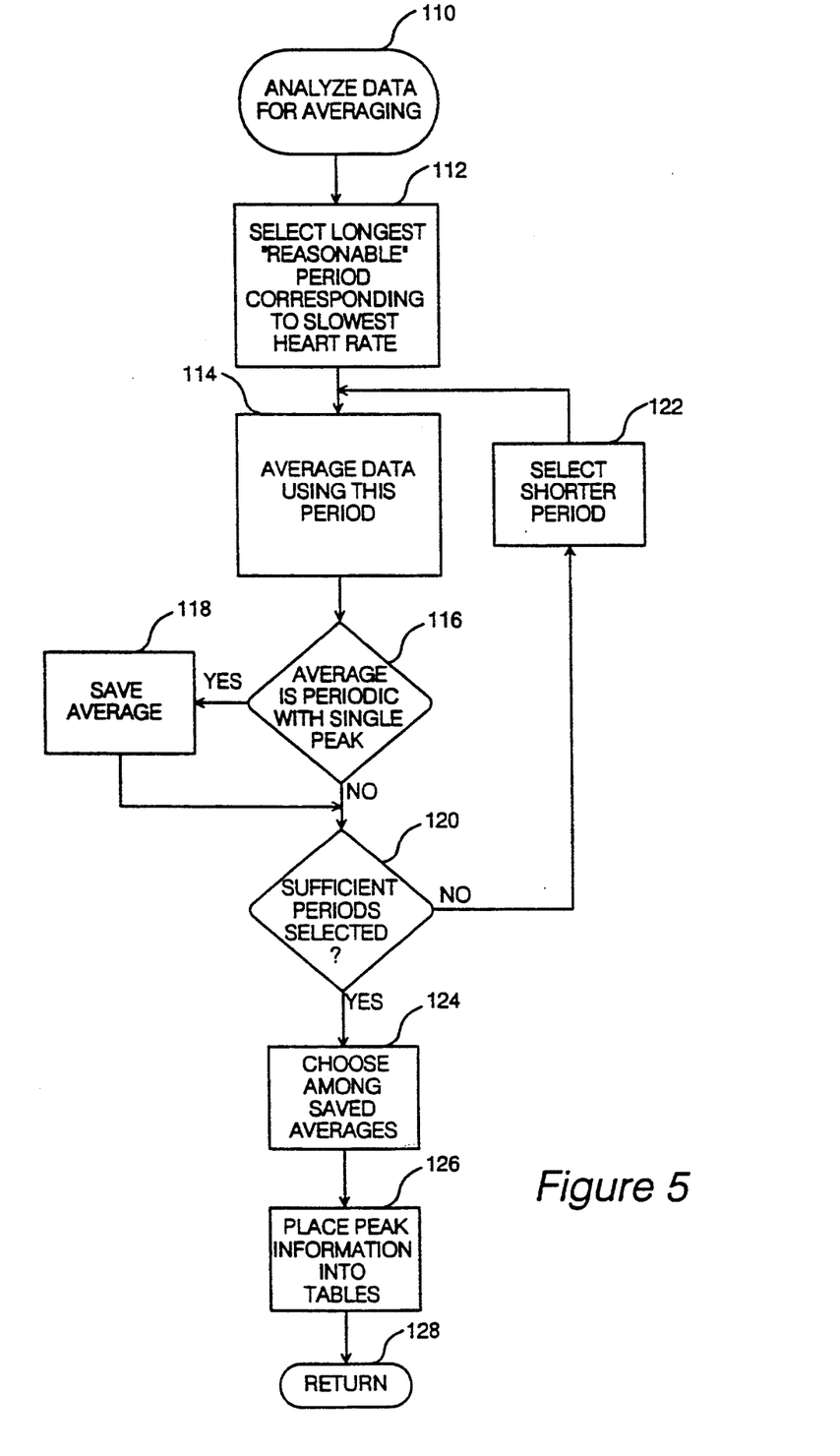
FIG. 5 is one embodiment of a data analysis subroutine called by the signal averaging subroutine shown in FIG. 4.

A subroutine for analyzing the data stored at step 98 is shown in FIG. 5. The routine starts at 110. At step 112, the routine selects the longest "reasonable" period between subsequent heart beats, which would correspond to the slowest reasonable heart rate. A reasonable range of rates can be either the range of physiological possible heart rates for a given patient population or it could be calculated from a given patient. Reasonable rates can be defined as a function of heart rates previously measured on a patient.

Figure 7A:
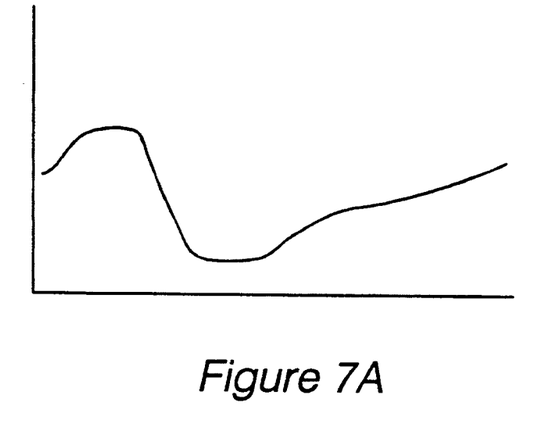
FIGS. 7A and 7B are graphs illustrating periodic waveforms as that term is used to describe the inventive blood pressure monitor.
Figure 7B:
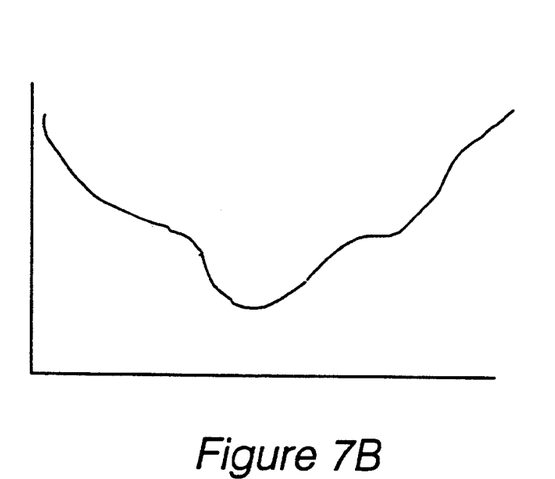
Figure 8A:
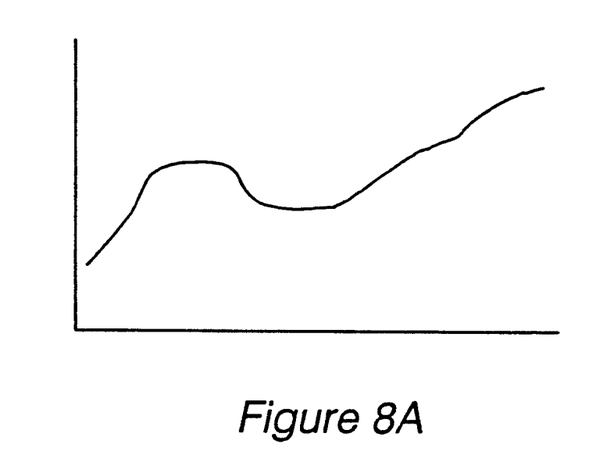
FIGS. 8A and 8B are graphs illustrating non-periodic waveforms as that term is used to describe the inventive blood pressure monitor.
Figure 8B:
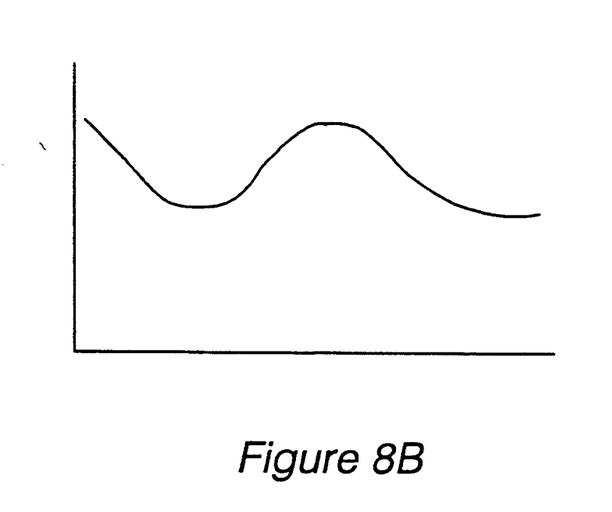

An average waveform is calculated at step 114 using the selected period, just as if a trigger had been detected at that period. In other words, if the selected period is 2 seconds, then the subroutine assumes that a trigger is generated every 2 seconds, and that samples taken at $t_0$, $2+t_0$, $4+t_0$, etc. are assumed to be corresponding samples of successive oscillometric pulses, and they are thus summed with each other to generate a sample average. The sample average for each sample point is calculated in the same manner to generate an average waveform. A decision is made at step 116 as to whether this average waveform is to be saved or to be discarded. To be saved, the average waveform must be periodic; i.e., the last value of the average waveform must be approximately equal to the first value of that average waveform. FIGS. 7A and 7B show examples of periodic average waveforms, while FIGS. 8A and 8B show examples of average waveforms which are not periodic.

An additional criteria may be used at step 116 to save or reject the average waveform. For example, the average waveform might be rejected unless is has a single major peak. There are many conventional algorithms that identify peaks within a waveform. However, the subroutine of FIG. 5 would still function without the use of this additional criteria.

If an average waveform meets the criteria for being saved at 116, the program branches to 118 where the average waveform is saved. If the criteria are not met at 116, the program branches to 120 causing the average waveform to be lost.

At 120, the program decides whether or not a sufficient number of rates have been selected. The first time decision box 120 is reached, the answer will be "NO"; so the program will branch to step 122 where the next shorter period will be selected. The same data will now be averaged at 114 assuming that a shorter period occurs between successive triggers. For example, the subroutine may assume that the period between successive triggers is 1.8 seconds. Thus, samples taken at $t_0$, $1.8+t_0$, $3.6+t_0$, etc. are assumed to be corresponding samples of successive oscillometric pulses, and they are thus summed with each other to generate a sample average. The sample average for each sample point is calculated in the same manner to generate an average waveform. The subroutine once again determines at step 116 whether the average waveform generated using the new period is to be saved or to be discarded. If the average waveform is to be rejected, the next short period will be selected once again at step 122.

Each time an average waveform is saved, the subroutine checks at step 120 whether a sufficient number of periods between assumed triggers have been tested. There are many ways to decide whether or not a sufficient number of periods have been tested. For example, the following methods could be used:

1. All "physiologically reasonable" rates could be selected. However, a more economical algorithm will probably be preferred.
2. The rates can be limited to those similar to previous rates for the given subject.
3. The rates can be selected until one or more averages are saved.

Eventually a sufficient number of rates will have been tested. Then the routine will branch from 120 to 124, where the routine will choose among the several averages saved. The choice will be made as a function of template matching. The shape and amplitude of the "expected" oscillometric pulse are known. The program will use a conventional algorithm for comparing a waveform to a template. The average that most closely matches the template will be chosen as the true oscillometric pulse for the given pressure step.

Once the average waveform is chosen, the program extracts and stores information about the peak at 126 before returning at 128.

Figure 6:
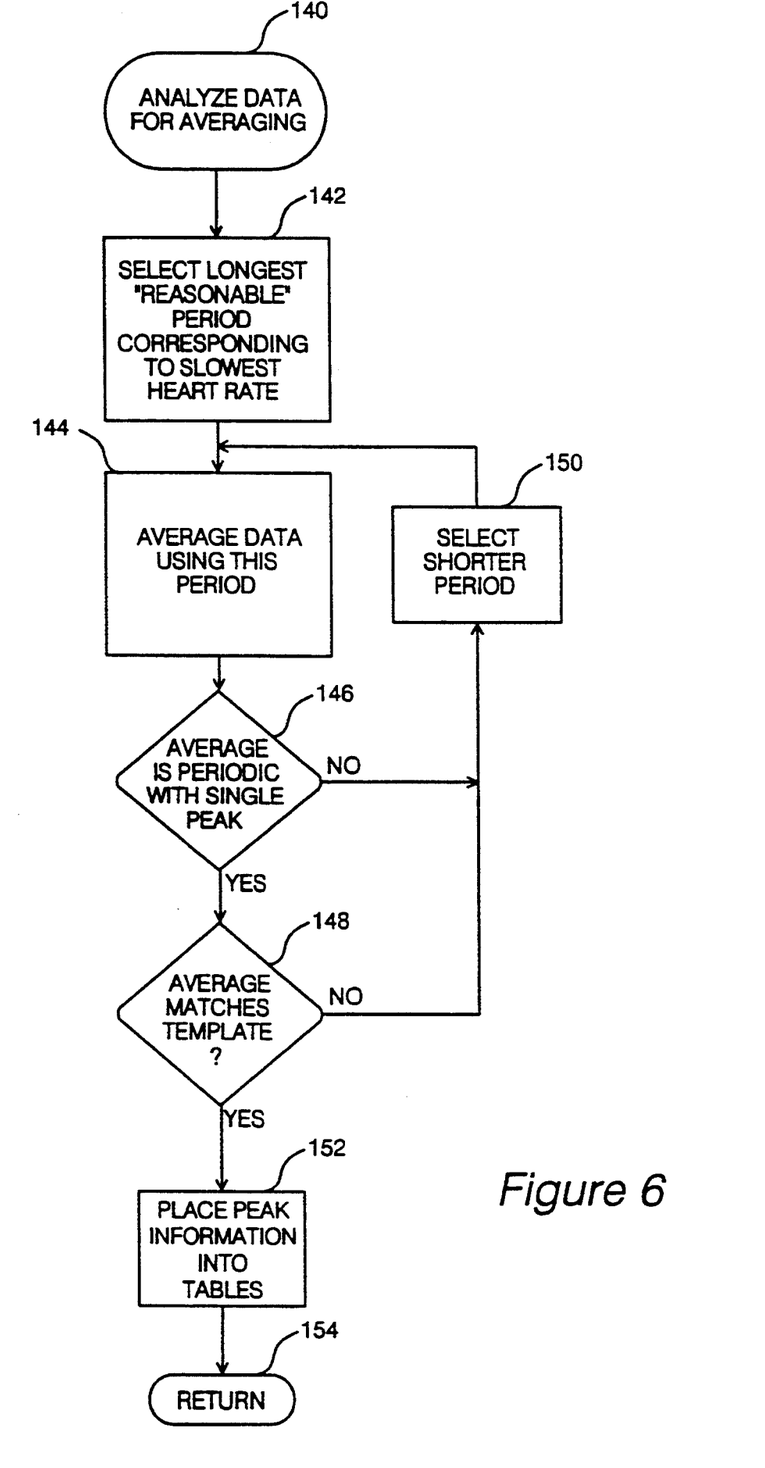
FIG. 6 is another embodiment of a data analysis subroutine called by the main computer program shown in FIG. 2.

An alternative subroutine for analyzing data for averaging is illustrated in FIG. 6. It should be realized that the subroutine of FIG. 6 is merely a slight modification of the subroutine of FIG. 5, and many such modifications are possible without departing from the present invention. In the same manner as the subroutine of FIG. 5, the subroutine of FIG. 6 is entered at 140, the longest period is selected at 142 and an average is calculated at 144. A test performed at step 146 to determine if the average calculated at 144 is periodic with a single peak is also identical to the corresponding step 116 performed in the subroutine of FIG. 5. However, the subroutine of FIG. 6 differs from the subroutine of FIG. 5 by performing a second test to compare the just calculated waveform to a template. This test is immediately performed at step 148. If either the test at step 146 or the test at step 148 fails, then the program branches to step 150 were a shorter period is selected for the next calculation of an average. If both test performed at steps 146 and 148 pass, the information about the peak is placed into the tables at step 152. Thus, while the comparison between the average waveforms and the template occurs in at step 124 of FIG. 5, the same comparison occurs at step 148 of FIG. 6. The subroutine then returns to the calling routine at 154.

The second embodiment of the signal averaging subroutine shown in FIGS. 5 and 6 can be more fully illustrated by the use of the exemplary data in the tables below. The raw data are the same as that previously averaged using the triggers. However, in this case the triggers are no longer available.

| SAMPLES | 2 | 3 | 7 | 5 | 4 | 3 | 8 | 3 | 4 | 7 | 3 |
|---|---|---|---|---|---|---|---|---|---|---|---|
| | | | | 4 | | | | | | | |

For this illustration, we will assume that the only "reasonable" periods are 5, 4 and 3. The following three tables can be constructed using these three periods.

The first table calculates an average using a period of 5 as follows:

TABLE 2

| | | | | | |
|---|---|---|---|---|---|
| 1ST 5 SAMPLES | 2 | 3 | 7 | 5 | 4 |
| 2ND 5 SAMPLES | 3 | 8 | 3 | 4 | 7 |
| 3RD 5 SAMPLES | 3 | 4 | | | |
| AVERAGE | 2.6 | 5.0 | 5.0 | 4.5 | 5.5 |

It is apparent from an examination of Table 2 that the average is not periodic in that the first entry is not approximately equal to the last entry.

The second table calculates the average using a period of 4 as follows:

TABLE 3

| | | | | |
|---|---|---|---|---|
| 1ST 4 SAMPLES | 2 | 3 | 7 | 5 |
| 2ND 4 SAMPLES | 4 | 3 | 8 | 3 |
| 3RD 4 SAMPLES | 4 | 7 | 3 | 4 |
| AVERAGE | 3.3 | 4.3 | 6.0 | 4.0 |

The last entry of 4.0 is sufficiently close to the first entry of 3.3 that the average waveform can be considered periodic.

The final table calculates an average using a period of 3 samples as follows:

TABLE 4

| | | | |
|---|---|---|---|
| 1ST 3 SAMPLES | 2 | 3 | 7 |
| 2ND 3 SAMPLES | 5 | 4 | 3 |
| 3RD 3 SAMPLES | 8 | 3 | 4 |
| 4TH 3 SAMPLES | 7 | 3 | 4 |
| AVERAGE | 5.5 | 3.25 | 4.5 |

In this example, the last entry of 4.5 is also sufficiently close to the first entry of 5.5 that the average waveform can be considered periodic. Thus, the use of periods of both 4 and 3 will produce periodic average waveforms. The subroutine must then choose which of these two suitable candidates should best be used. It performs this choice by looking for which average waveform has a single positive peak. The average waveform using a period of 4 samples has a single positive peak (value above the average value) while the average waveform using a period of 3 samples has a trough (a value lower than the average value). Therefore, the average using 4 samples more closely matches the template, and the subroutine will choose the average waveform calculated using a period of 4 samples over the average using a period of 3 samples.

I claim:

1. In a method for using a blood pressure monitor of the type having a blood pressure cuff: an air pump in fluid communication with said cuff to direct pressurized air into said cuff, an air valve in fluid communication with said cuff to selectively vent said cuff to atmosphere, a pressure transducer in fluid communication with said cuff generating an output including a pressure signal indicative of a steady state fluid pressure in said cuff corresponding to an occlusive pressure exerted by said cuff on an artery and a transient fluid pressure in said cuff indicative of an amplitude of an oscillometric waveform, a processor in electrical communication with said air pump and said air valve for selectively energizing said air pump or valve to pressurize or depressurize said cuff respectively comprising:

(a) setting the steady state fluid pressure in said cuff to an initial value:

(b) sampling the output of said transducer over a plurality of heartbeats to generate samples of said oscillometric waveform;

(c) prior to identifying the existence of an oscillometric pulse during any period of time, summing the samples of said transducer output taken after one heartbeat with the samples of said transducer output taken at corresponding times after a plurality of other heartbeats to obtain composite samples of said oscillometric waveform over a plurality of heartbeats, said composite samples corresponding to an average oscillometric waveform:

(d) storing said composite samples:

(e) altering the steady state fluid pressure in said cuff;

(f) repeating steps (b)–(e) a plurality of times; and (g) analyzing said average oscillometric waveforms to determine blood pressure.

2. The method of claim 1 wherein said composite samples are generated by the steps of:

generating a plurality of trigger signals each of which has a predetermined temporal relationship to a respective heartbeat; and summing the said transducer output samples taken after each trigger signal with correspondingly ordered transducer output samples taken after respective other trigger signals.

3. The method of claim 2 further including the step of dividing each of said composite samples by the number of transducer output samples that have been summed to generate said composite sample so that each of said composite samples is an average of the samples taken at the same time after each of said trigger signals.

4. The method of claim 2 wherein said composite samples are generated by the steps of:

(a) periodically sampling the output of said pressure transducer;

checking for the occurrence of said trigger signal;

(c) discarding each sample of said pressure transducer samples until said trigger signal occurs;
(d) summing the pressure transducer samples taken after said trigger signal occurs for a predetermined period after the occurrence of said trigger signal with correspondingly ordered pressure transducer samples previously taken after respective other trigger signals; and
(e) repeating steps a–d for a plurality of trigger signals.

5. The method of claim 2 wherein the output of said transducer is sampled for a predetermined number of heartbeats after each trigger signal during each value of steady state fluid pressure.

6. The method of claim 2 wherein the number of heartbeats during which the output of said transducer is sampled at each value of steady state fluid pressure in said cuff is determined by the steps of:
comparing a composite sample derived after each heartbeat with a corresponding composite sample derived after a previous heartbeat; and
continuing to sample the output of said transducer and derive composite samples during successive heartbeats until the difference between the composite sample derived after a heartbeat and the corresponding composite sample derived after the previous heartbeat is less than a predetermined value.

7. The method of claim 1 wherein said composite samples are generated by the steps of:
(a) storing said transducer output samples for a plurality of heartbeats;
(b) assuming that a period between heartbeats is an initial value;
(c) summing stored transducer output samples having the same temporal relationship with the start of each assumed period, thereby deriving tentative composite samples;
(d) evaluating said tentative composite samples to determine if they correspond to an actual oscillometric waveform, thereby determining that the assumed period is an actual period between heartbeats;
(e) if the assumed period is the actual period between heartbeats, adopting said tentative composite samples as said composite samples that are analyzed to determine blood pressure; and
(f) if the assumed period is not the actual period between heartbeats, altering the assumed period between heartbeats and repeating steps c–f.

8. The method of claim 7 wherein said tentative composite samples are evaluated in step (d) by determining if the oscillometric waveform corresponding to said tentative composite samples is periodic.

9. The method of claim 8 wherein said tentative composite samples are further evaluated in step (d) by determining if the oscillometric waveform corresponding to said tentative composite samples has a single major peak.

10. The method of claim 7 wherein said tentative composite samples are evaluated in step (d) by comparing to said tentative composite sample to a template of samples corresponding to an actual oscillometric waveform.

11. The method of claim 7 further including the step of dividing each of said composite samples by the number of transducer output samples that have been summed to generate said composite sample so that each of said composite samples is an average of the transducer output samples taken at the same time after the start of each assumed period.

12. A blood pressure monitor, comprising:
a blood pressure cuff:
an air pump in fluid communication with said cuff to direct pressurized air into said cuff:
an air valve in fluid communication with said cuff to selectively vent said cuff to atmosphere:
a pressure transducer in fluid communication with said cuff generating an output including a pressure signal indicative of a steady state fluid pressure in said cuff corresponding to an occlusive pressure exerted by said cuff on an artery and a transient fluid pressure in said cuff indicative of an amplitude of an oscillometric waveform;
an analog-to-digital converter connected to said transducer sampling the output of said transducer and generating respective digital samples corresponding to the output of said transducer when said samples are taken: and
processor means in electrical communication with said analog-digital converter said air pump and said air valve for energizing said air pump and said air valve to set the steady state fluid pressure to a plurality of pressure values, said processor means summing digital samples taken after one heartbeat with digital samples taken at corresponding times after a plurality of other heartbeats to obtain composite samples of said oscillometric waveform over a plurality of heartbeats prior to identifying the existence of an oscillometric pulse during any period of time, and analyzing said composite samples at a plurality of different steady state fluid pressures in said cuff to determine blood pressure.

13. The blood pressure monitor of claim 12 wherein said blood pressure monitor further includes a trigger signal generator connected to said processor means for producing a trigger signal having a predetermined temporal relationship to each heartbeat, and wherein said processor means derives said composite samples by summing said digital samples taken after each trigger signal with correspondingly ordered digital samples taken after respective other trigger signals.

14. The blood pressure monitor of claim 13 wherein said processor means further divides each of said composite samples by the number of digital samples that have been summed to generate said composite sample so that each of said composite samples is an average of the samples taken at the same time after each of said trigger signals.

15. The blood pressure monitor of claim 13 wherein said processor means sums said digital samples only for a predetermined period after the occurrence of each trigger signal.

16. The blood pressure monitor of claim 13 wherein said processor means determines blood pressure by summing said digital samples during a predetermined number of heartbeats at each of a plurality of different steady state fluid pressures in said cuff.

17. The blood pressure monitor of claim 13 wherein said processor means sums said digital samples at each steady state fluid pressure in said cuff until the difference between a composite sample derived after a heartbeat and the corresponding composite sample derived after a previous heartbeat is less than a predetermined value.

18. The blood pressure monitor of claim 12, wherein said blood pressure monitor further includes memory means for storing said digital samples for a plurality of heartbeats, and wherein said processor means determines blood pressure by sequentially deriving sets of tentative composite samples each of which correspond to the sum of digital samples having the same temporal relationship with the start of a respective assumed period between heartbeats until the waveform corresponding to a set of tentative composite samples for an assumed period correspond to an actual oscillometric waveform, said processing means then determining blood pressure by analyzing the tentative composite samples corresponding to the actual oscillometric waveform.

19. The blood pressure monitor of claim 18 wherein said processing means determines that a set of tentative composite samples for an assumed period correspond to an actual oscillometric waveform by determining if the oscillometric waveform corresponding to said tentative composite samples is periodic.

20. The blood pressure monitor of claim 19 wherein said processing means does not determine that a set of tentative composite samples for an assumed period correspond to an actual oscillometric waveform unless said tentative composite samples further correspond to an oscillometric waveform having a single major peak.

21. The blood pressure monitor of claim 18 wherein said processing means determines that a set of tentative composite samples for an assumed period correspond to an actual oscillometric waveform by comparing said tentative composite samples to a template of samples corresponding to an actual oscillometric waveform.

22. The blood pressure monitor of claim 18 wherein said processor means further divides each of said composite samples by the number of digital samples that have been summed to generate said composite sample so that each of said composite samples is an average of the digital samples taken at the same time after the start of each assumed period.

* * * * *

UNITED STATES PATENT AND TRADEMARK OFFICE
CERTIFICATE OF CORRECTION

PATENT NO. : 5,337,750

DATED : August 16, 1994

INVENTOR(S) : Richard A. Walloch

It is certified that error appears in the above-identified patent and that said Letters Patent is hereby corrected as shown below:

In column 12, claim 1, line 28, after "respectively" and before "comprising", please insert --said method--.

In column 14, claim 12, line 23, please delete "analog-digital" and substitute therefor --analog-to-digital--.

Signed and Sealed this

Twentieth Day of December, 1994

Attest:

BRUCE LEHMAN

Attesting Officer

Commissioner of Patents and Trademarks